United States Patent
Scholl

[11] Patent Number: 5,836,307
[45] Date of Patent: Nov. 17, 1998

[54] CONTRACEPTIVE SHEATH

[76] Inventor: Thomas Scholl, 14, Quai Kleber, F-67000 Strassbourg, France

[21] Appl. No.: 481,427
[22] PCT Filed: Dec. 17, 1993
[86] PCT No.: PCT/DE93/01214
  § 371 Date: Sep. 20, 1995
  § 102(e) Date: Sep. 20, 1995
[87] PCT Pub. No.: WO94/13231
  PCT Pub. Date: Jun. 23, 1994
[51] Int. Cl.⁶ ............................................. A61F 5/44
[52] U.S. Cl. ............................................. 128/844; 128/918
[58] Field of Search .................... 128/842, 844, 128/918; 604/347–353

[56] References Cited

U.S. PATENT DOCUMENTS 2,348,773  5/1944  Wyman ................................. 128/844
4,798,600  1/1989  Meadows .............................. 128/844
4,846,197  7/1989  Benjamin ............................. 128/844
5,109,871  5/1992  Thornton .

FOREIGN PATENT DOCUMENTS 1566365  4/1971  Germany .
2202462  7/1973  Germany .
4130220  12/1992  Germany .
513644  11/1971  Switzerland .

*Primary Examiner*—Michael A. Brown
*Attorney, Agent, or Firm*—Collard & Roe, P.C.

[57] ABSTRACT

A process is disclosed for producing a contraceptive sheath that is subdivided into two sections. The sections are delimited by a boundary line. The process is characterized in that the sheath is produced with its particularities in at least the immersion step with no further vulcanization steps. The boundary line is reinforced by the same elastic material and has a smaller diameter than the remaining elongated cylindrical part, so that the sheath is reliably retained in its original position.

12 Claims, 3 Drawing Sheets

CONTRACEPTIVE SHEATH

The present invention deals with a procedure for the production of a contraceptive sheath for contraception, especially a contraceptive sheath which guarantees a secure hold on the erected penis of the man.

Such a contraceptive sheath is already known from DE-OS 166 365. The contraceptive sheath known from the state of the art reveals at a certain point in the upper part of the contraceptive sheath an elastic rubber ring, which is put in a deepening groove in the immersion form either by hand or machine and then the actual contraceptive sheath is put on the immersion form. The ringshaped product can be vulcanised either on the inner or outside. Such a ring is regarded as disturbing during use and moreover is large-scale and cost-intensive in production.

Therefore it is the object of the present invention to put at disposal a procedure for production of a contraceptive sheath, which is easy and cheap in production and which meets the requirements of the approving authorities.

This task, is solved by the characterising features of the main claim.

According to the overall term of claim 1 the inventive procedure stands out in that the constricted forming of the immersion tool is defined in the middle by a ring groove, in which the elastic material of at least one immersion bath in at least one immersion process flows in the ring groove of the immersion tool and therefore effects an integrated greater material strength at the place of the constricted forming.

An advantage of the inventive procedure is that the elastic material flows in a ring groove at the upper part of the immersion tool during immersion and the ring groove represents a closed curve. Thereby an integrated greater material strength is effected at the place of the constricted forming. A further essential inventive advantage is that no large-scale vulcanisation steps are required, which firmly connect the elastic ring with the rest of the material.

As a consequence of the above mentioned advantages the person applying it has a great application advantage, which makes the inventive contraceptive sheath pleasant for usage, gives it a strong hold when used, no roughness disturbs on the surface, as is the case with those contraceptive sheaths known, from the state of the art.

An important advantage of the present invention has to be seen in the fact that the prophylactic according to the invention assures a safe fit during use, and that the constricting shaping does not produce any annoying roughness on the surface of the prophylactic.

It has been Found to be advantageous if the constricting shaping is approximately adapted to the shape of the glans of the male penis. However, such a form of constriction is not necessarily required, so that any other desired polygonal form of constriction can be selected provided it is closed within itself.

The fact that the front section of the prophylactic has a larger diameter than the rear section has to be viewed as another advantage, which means that a certain hollow space is formed between the glans of the male penis and the prophylactic.

With the prophylactic where the constricting shaping is adapted to the shape of the glans of the male penis, it has been found to be particularly advantageous that a marking is provided in a predetermined site of the rolled-up prophylactic, which shows the user the position of the shaping.

Additional advantages and developments are contained in the dependent claims.

The invention is explained in the following in greater detail by reference to the drawings, in which.

Figure 1:
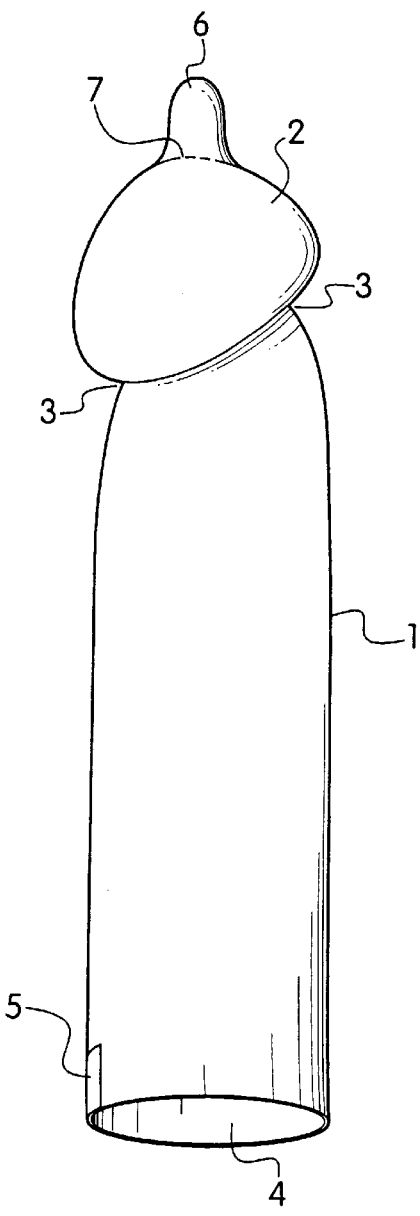
FIG. 1 shows the lateral view of a prophylactic according to the invention, in connection with which the shaping is adapted to the glans of the male penis.

FIG. 1 shows a prophylactic according to the invention which substantially consists of the two sections 1 and 2. The one end of the section 1 has an opening 4, whereas the other end is terminated by the constricting shaping on the boundary 3. Following the section 1, the section 2 is added. Now, according to the invention, the sections 1 and 2 are delimited by the boundary line 3. Said boundary line 3 has a slightly smaller diameter than the other, long-stretched-out cylindrical section 1. It is also smaller than the diameter of the front section 2. This necessarily results in a constricting shaping in the front part of the long-stretched-out, cylindrical part.

A reinforcing elastic material is to be applied along the boundary line 3, so that a firm, safe seating of the entire prophylactic on the erected penis of the male is assured in this way.

By the constricting shaping, therefore, the prophylactic is divided into two sections and narrowed at the same time along the boundary line 3. Such narrowing may have a diameter, for example of 3 cm if the section 1 or section 2 has a diameter of 3.5 cm. During intercourse, such constriction gets to be placed behind the edge of the glans of the male penis and maintains the entire prophylactic in its original, mounted position. In this way, the foreskin of the penis is prevented from slipping under the prophylactic covering the glans, which heretofore has been perceived as an annoying interference during intercourse.

So that the position of the shaping of the boundary line 3 of the rolled-up prophylactic can be readily recognized, a marking is provided on the edge of the roll, which may be a colored line in the simplest case. Conceivable are also small elevations in the material of the prophylactic.

Owing to the fact that the front section 2 may be slightly widened, mounting of the prophylactic on the penis of the male is largely facilitated.

Figure 2:
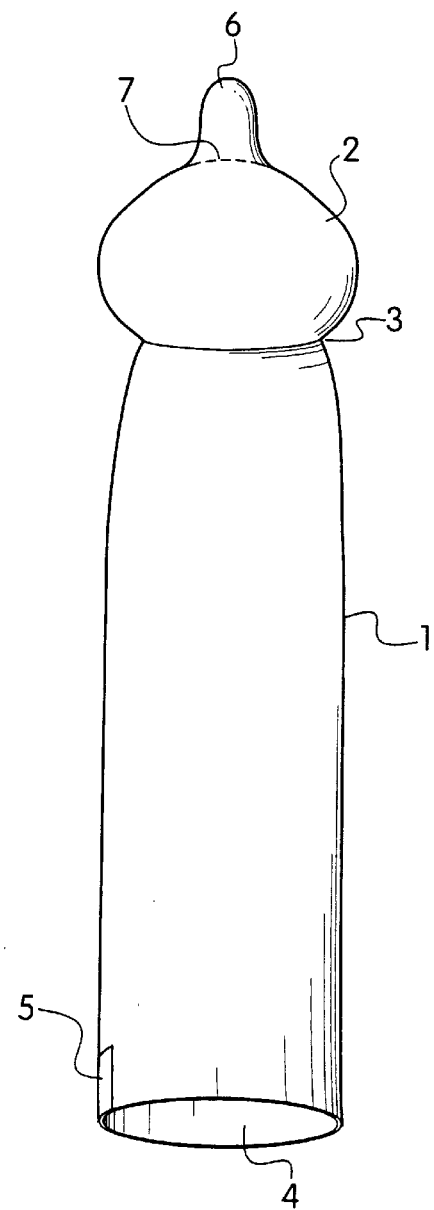
FIG. 2 shows the lateral view of a prophylactic according to the invention, in connection with which the boundary line between the front and rear parts is circular.

FIG. 2 shows another variation of the prophylactic according to the invention. However, it is different only in that the constricting boundary line 3 is not adapted to the natural shape of the glans of the male penis, but rather assumes a circular shape, which is reinforced by elastic material as well.

The front section 2 can be selectively terminated by a bulge 6 or a rounding 7. The other parts of this embodiment of the invention correspond with those described in FIG. 1.

Figure 3:
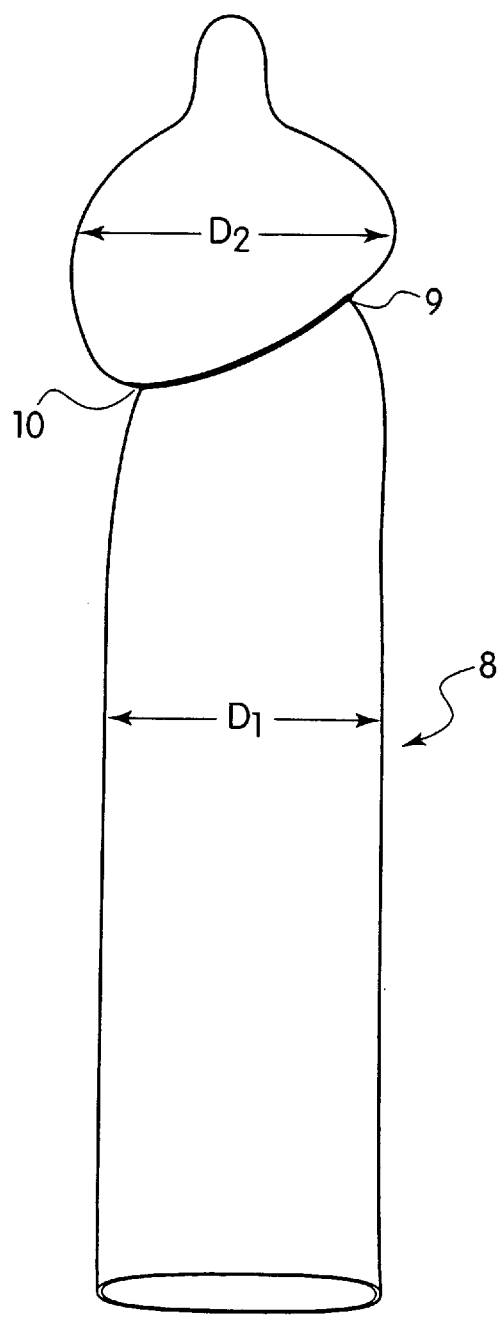
FIG. 3 shows a lateral view of the immersion tool (8)
Figure 4:
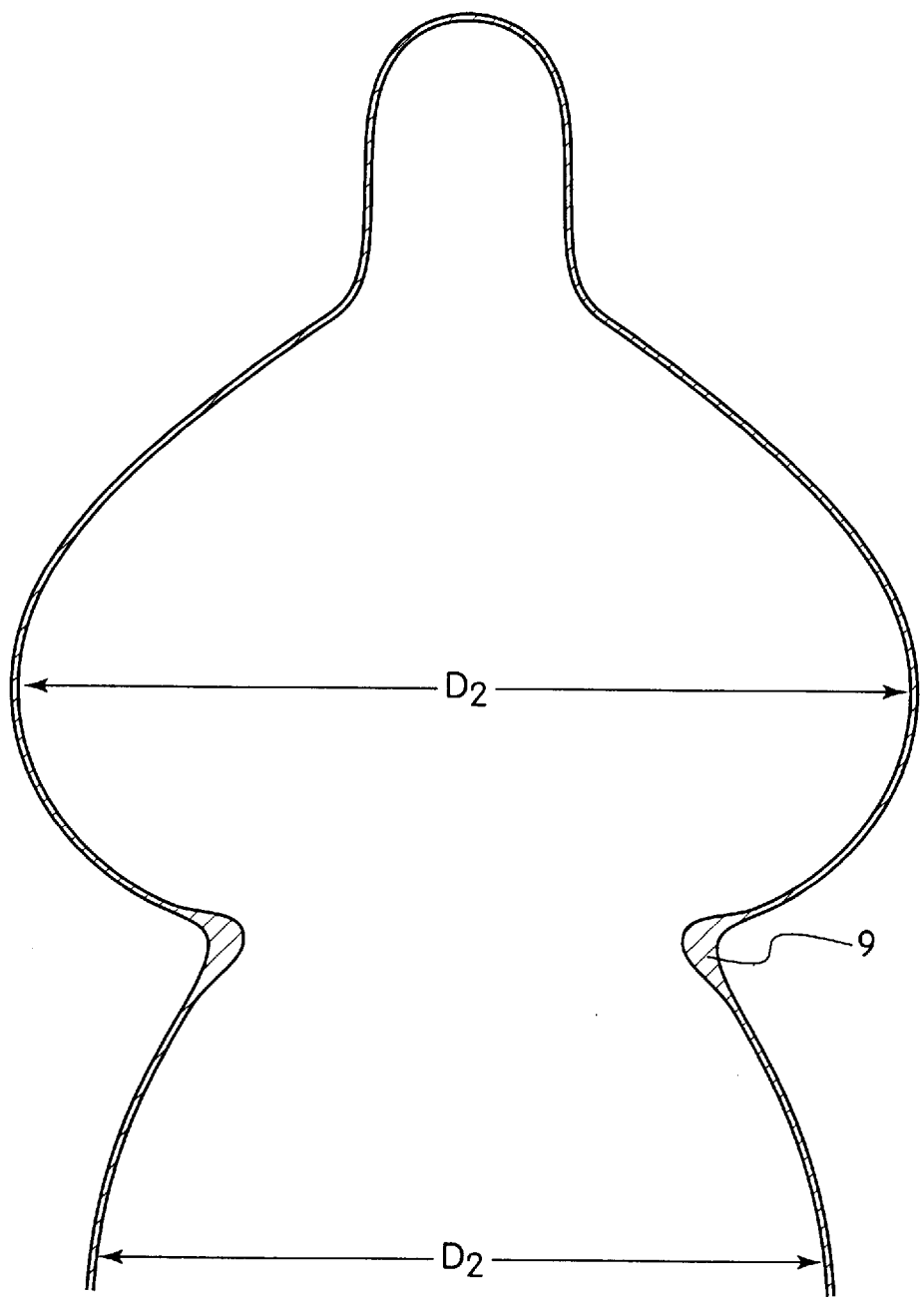
FIG. 4 shows an enlarged section of the immersion tool (8).

FIGS. 3 and 4 show an immersion tool 8 according to the invention, via which the elastic material is applied in the immersion process, which is known per se. Said tool 8 has the special shape of the finished product made of elastic material. The diameter (D1) of the first section 1 is, in this connection, smaller than the diameter (D2) of the second section 2 at the top end of the shaping tool. A groove 9 is present in the constriction 1, which is already visible, such groove extending around the entire shaft of the tool. The groove 9 is formed in such a way that in the course of the immersion process, the immersion material is applied in a greater amount especially in said groove, so that an externally smooth reinforcement of the elastic material is obtained in this site, as can be seen in FIG. 4, whereby the dark part represents the reinforcement of the elastic material.

I claim:

1. Procedure for the production of a contraceptive sheath, by the immersion process, said sheath comprising a thin-sided form part made of elastic material, of which one end is closed and another end is open, whereby a cylindrical elongated part is connected to the open end, which cylindrical part is subdivided into two sections and shows a constrictive forming in a front part of the cylindrical elongated part near the closed end as conclusion of the front part, whereby the constrictive forming is a curve which closes on itself, using an immersion tool to carry out the constrictive forming, comprising the steps of:

impressing the constrictive forming around the immersion tool at its deepest point by a special ring groove, wherein the elastic material flows in said ring groove during the immersion process, thereby producing an integrated greater strength of the material located at the constrictive forming.

2. The procedure according to claim 1, wherein the constricted forming in the immersion tool is made in a way that it results on the inner and outside in a smooth curve stream at the border from the front to the end sections on both sides.

3. The procedure according to claim 1, wherein the constricted forming is adapted to the form of the glans of the penis of a man.

4. The procedure according to claim 1, wherein the constricted forming is circular.

5. The procedure according to claim 1, wherein the length and the diameter of the front and end sections are adapted to the average diameter length and average diameter of the penis of a man.

6. The procedure according to claim 1, wherein the front section has a greater diameter than the end section.

7. The procedure according to claim 1, wherein the front and the end sections show the same diameters.

8. The procedure according to claim 1, wherein the front closed section has a bulge at the end.

9. Prophylactic comprising a cylindrical, elongated, thin-walled sheath of elastic material having a closed end and an open end, said sheath being divided into two sections, which are a front section and a rear section with a border between said sections; said border being a constriction shape adjusted to the shape of a glans of a male penis, said border having a wall thickness being greater than wall thickness of the front section and the rear section;

said border constriction shape having an enveloping curve which is a constant curve;

said constriction shape being a reinforcement of the elastic material and being of the same material as the front section and the rear section so that the surface of the sheath extends smoothly on an inside surface and an outside surface at a transition from the front section to the rear section;

said front section having a larger diameter than the rear section; and said prophylactic has a marking visible in a rolled-up condition in order to orient a user regarding the position of the constriction shape.

10. Prophylactic according to claim 9, wherein the constriction shape is circular.

11. Prophylactic according to claim 9, wherein the constriction shape is a polygon form which is a curve closed on itself.

12. Prophylactic according to claim 9, wherein the front section is a closed section which is provided with a bulge at the end.

* * * * *